(12) United States Patent
Platt

(10) Patent No.: US 6,245,316 B1
(45) Date of Patent: *Jun. 12, 2001

(54) ENHANCEMENT OF DELIVERY OF RADIOIMAGING AND RADIOPROTECTIVE AGENTS

(76) Inventor: David Platt, 12 Appleton Cir., Newton, MA (US) 02159

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/167,685

(22) Filed: Oct. 7, 1998

Related U.S. Application Data

(60) Provisional application No. 60/061,371, filed on Oct. 8, 1997.

(51) Int. Cl.[7] .......................... A61K 51/00; A61M 36/14
(52) U.S. Cl. .................. 424/1.73; 424/1.11; 424/1.65; 424/9.3; 424/9.1; 534/14
(58) Field of Search .................. 424/1.11, 1.65, 424/1.73, 1.81, 9.1, 9.3, 9.35, 9.4, 9.43, 9.5, 9.6, 9.7, 9.8; 534/7, 10–16; 127/30; 514/23; 436/95; 536/4.1

(56) References Cited

U.S. PATENT DOCUMENTS

| | | | |
|---|---|---|---|
| 4,439,414 | 3/1984 | Shiue et al. | 424/1.1 |
| 4,789,542 | 12/1988 | Goodman et al. | 424/1.1 |
| 4,826,966 | 5/1989 | Goodman et al. | 536/18.4 |
| 5,141,739 | 8/1992 | Jung et al. | 424/4 |
| 5,167,947 | 12/1992 | Geary | 424/11 |
| 5,262,425 | 11/1993 | Farr et al. | 514/299 |
| 5,336,506 | 8/1994 | Josephson et al. | 424/488 |
| 5,478,576 | 12/1995 | Jung et al. | 424/488 |
| 5,554,386 | 9/1996 | Groman et al. | 424/488 |
| 5,582,172 | 12/1996 | Papisov et al. | 128/653.4 |
| 5,679,318 | * 10/1997 | Vanderheyden et al. | |
| 5,783,171 | 7/1998 | Gustavson et al. | 424/1.73 |
| 5,843,403 | 12/1998 | Dean | 424/1.73 |

* cited by examiner

Primary Examiner—Dameron L. Jones
(74) Attorney, Agent, or Firm—Gifford, Krass, Groh, Sprinkle, Anderson & Citkowski, P.C.

(57) ABSTRACT

A radioimaging material or a radioprotective material is attached to a carbohydrate which is capable of binding to or penetrating a cell. The carbohydrate material can be preferentially taken up by tumor cells and provides for imaging thereof.

5 Claims, 1 Drawing Sheet

ENHANCEMENT OF DELIVERY OF RADIOIMAGING AND RADIOPROTECTIVE AGENTS

RELATED APPLICATION

This patent application claims priority of provisional patent application Ser. No. 60/061,371 filed Oct. 8, 1997, also entitled "Enhancement of Delivery of Radioimaging and Radioprotective Agents."

FIELD OF THE INVENTION

The invention relates to novel compositions and methods for enhancing delivery of radioimaging and radioprotective agents.

BACKGROUND OF THE INVENTION

A radioimaging agent is administered for the purpose of visualizing various body tissues through the radiative properties of the agent, or the agent's interactions with high energy radiation. Computed axial tomography (CAT) and positron emission tomography (PET) are representative examples of radioimaging techniques currently in use for visualizing various physiological structures. Of particular interest is the imaging of in vivo tumors and the effects various therapeutics have on such a tumor. A radioimaging agent typically carries a radioactive tag or label that must reach a given organ that is being studied and must undergo a reaction or uptake that provides information related to the organ's condition or the presence of a tumor. For a radioimaging agent to be effective in visualizing tumors, malignant cells must differentially react with or uptake, an agent. Simple sugars and carbohydrates are major energy sources of cell metabolism and therefore represent a chemical structure well suited for modification into a radioimaging agent.

Polysaccharide based radioimaging and radioprotective agents are characterized by slow cellular uptake, owing to the size and transport mechanism of such large molecules. For example, U.S. Pat. No. 5,554,386 details the endocytosis of polysaccharide therapeutics. In contrast to polysaccharides, monosaccharides and disaccharides in general, and glucose in particular, cross cellular membranes by active transport and frequently in conjunction with ion transport associated with the membrane potential. Because of the high diffusion rates and active transport of mono- and disaccharides, these molecules are more readily internalized within cells.

There are a number of radioisotopes suitable for use as radioimaging agents. The choice of radioisotope depends on factors including: isotope lifetime, modes of decay, decay energy, particle emission energies and neutron capture cross-sections. Radioisotopes are selected for particular radioimaging tasks based on the compatibility of the radioisotope properties with the imaging detector system, storage requirements and toxicity. Since the toxicity typically decreases and cellular uptake rates increase by bonding the radioisotope to a suitable carrier, one must further balance the synthetic chemistry necessary to bond a selected radioisotope to a carrier molecule against the imaging properties of the selected radioisotope. Previous efforts have involved bonding radioisotopes of fluorine, carbon and iodine to glucose or glucose-like molecules; for example, see U.S. Pat. No. 4,789,542. Still other efforts have involved coating an inorganic core with carbohydrate molecules to facilitate cellular delivery; for example, see U.S. Pat. No. 5,582,172.

There is also an important need for radioprotective agents. A radioprotective agent functions to protect critical body tissues against low to moderate doses of ionizing radiation and the in situ generated free radicals associated with biological tissues being exposed to such radiation. Radioprotective agents are beneficially administered to patients receiving radioisotope and radiation treatments, as well as to protect individuals entering radiation contaminated environments. Such a radioprotective agent serves antimutagenic and anticarcinogenic roles within tissues containing such an agent. Delivery of radioprotective agents has previously proven to be a limiting factor in their use; for example, see U.S. Pat. No. 5,167,947. To this end, the mono- and disaccharides of the instant invention serve as effective carriers for radioprotective moieties.

BRIEF DESCRIPTION OF THE INVENTION

Disclosed herein is a pharmaceutical composition for enhancing the delivery of a radioimaging or radioprotective agent in vivo. The agent comprises a carbohydrate which is capable of binding to, or penetrating a target cell. The carbohydrate has attached thereto either a radioisotope or a free radical scavenger moiety, and the composition further includes a carrier suitable for delivery of the carbohydrate to the target cell. In some embodiments, the radioactive isotope is an isotope of technetium, carbon or gadolinium. In those instances where the composition includes a radical scavenger, the radical scavenger may comprise an aminoalkylaminoethyl phosphorothiolate.

The invention also includes a method of imaging a cancerous tumor which comprises contacting the tumor with a radiolabeled carbohydrate, allowing sufficient time for said carbohydrate to enter the tumor and recording a radioimage of the tumor using radioimaging techniques. In one preferred method, the carbohydrate comprises D-glucose. The invention further includes a method for delivering a bioactive radioprotectant to an animal which comprises binding the radioprotectant to a carbohydrate and administering it to the animal. One preferred carbohydrate comprises D-glucose and one preferred radioprotectant that comprises ethiofos or a metabolite thereof.

The invention further includes a radioimaging material comprising a glucoside of a radioisotope of gadolinium, and in one embodiment, the material comprises a radioisotope of gadolinium bonded to three molecules of glucose.

DETAILED DESCRIPTION OF THE INVENTION

Figure 1:
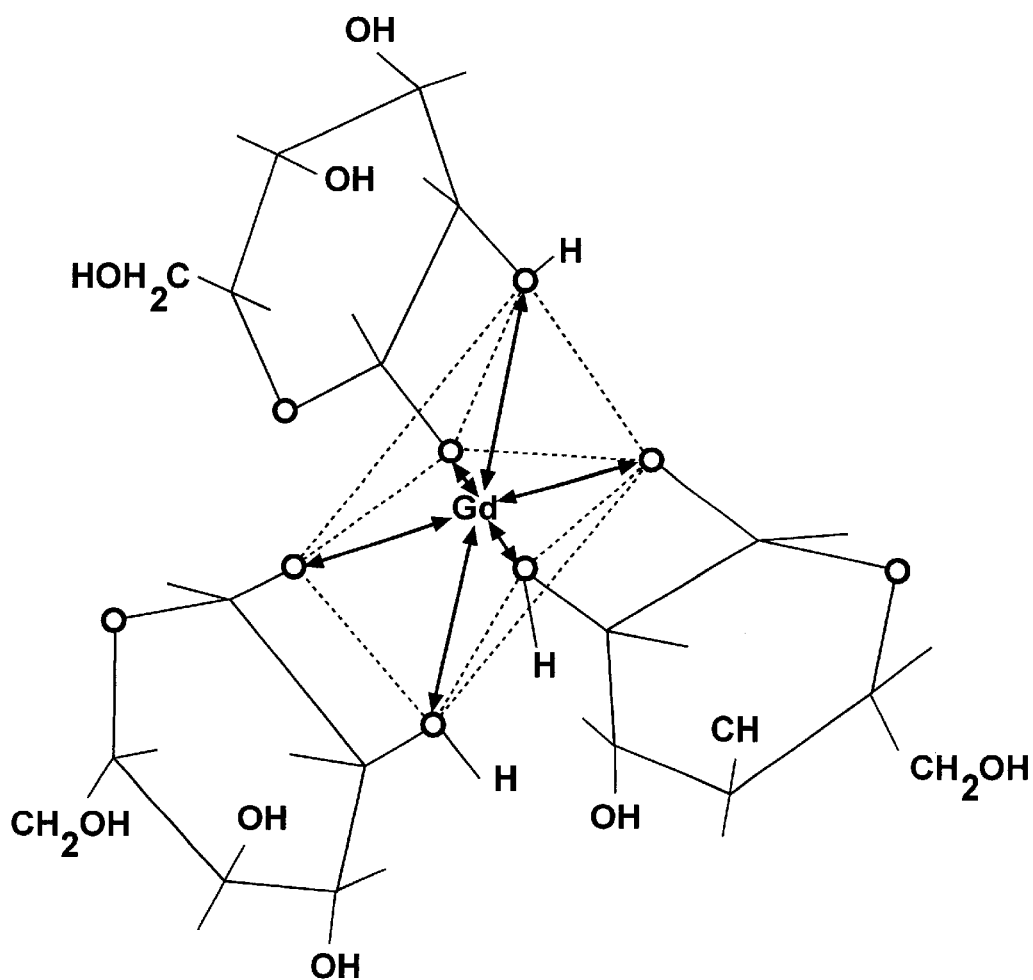
FIG. 1 is a molecular formula for a gadolinium glucoside of the present invention.

This invention provides enhanced delivery of radioimaging and radioprotective agents through the bonding of radioisotopes and radioprotective moieties to carbohydrates, thereby forming novel radioimaging and radioprotective molecules. The present invention has many advantages as compared to existing agents, including reduced toxicity and increased selectivity of cellular uptake. The present invention harnesses the ability of cells, and especially tumor cells, to accumulate carbohydrates from the bloodstream. The use of carbohydrates in general and monosaccharides, in particular, as carriers for radioisotopes and radioprotective moieties is the basis of the radioimaging and radioprotective methodologies detailed herein. Radioimaging agents are preferentially delivered to malignant cells based on the importance of carbohydrates as metabolites in cell function. As cell metabolism increases, the cellular uptake of carbohydrates similarly increases. Thus, a growing tumor mass accumulates a greater per cell percentage of available carbohydrates than surrounding, nonreplicating tissue.

Some radioisotopes that decay by positron emission, and which are amenable to bonding with carbohydrates to form radioimaging agents of the instant invention illustratively include $^{43}$Sc, $^{52}$Mn, $^{55}$Co, $^{61}$Cu, $^{64}$Cu, $^{66}$Ga, $^{66}$Ge, $^{72}$As, $^{73}$Se, $^{87}$Y, $^{85}$Zr, $^{86}$Zr, $^{87}$Zr, $^{89}$Nb, $^{90}$Nb, $^{90}$Mo, $^{11}$C and $^{99}$Tc. Negative beta radiation emitting isotopes amenable to bonding to carbohydrates so as to form radioimaging agents of the instant invention illustratively include: $^{27}$Mg, $^{28}$Mg, $^{47}$Sc, $^{56}$Mn, $^{65}$Ni, $^{66}$Ni, $^{67}$Cu, $^{159}$Gd and $^{162}$Gd. The radioisotope lifetime, energenics and radioimaging detection system are some of the important factors in the election of a particular radioisotope for application in radioimaging, and isotopes other than those listed herein may also be employed.

Radioisotopes bonded to carbohydrates that are operative in the instant invention are limited only by the requirement that they are capable of binding to, or penetrating a malignant cell. To this end, suitable biocompatible compounds that are operative in the instant invention as carriers illustratively include pentose monosaccharides, such as ribose, arabinose, xylose, lyxose; hexoses, such as allose, altrose, glucose, gulose, manose, idose, galactose, fructose, and tallose; disaccharides such as sucrose, maltose, cellubiose and lactose; polysaccharides such as cellulose and agarose; the pyranoses thereof; the furanoses thereof; the sugar alcohols thereof; and the dioxy sugars thereof. Preferably, the D enantiomers of carbohydrates are utilized, for reasons including cellular recognition and biocompatibility. More preferably, the carbohydrate is D-glucose. In some instances, the isotope is bonded to a single carbohydrate molecule, while in other instances, it may be bonded to several carbohydrate molecules.

The synthetic routes used to couple a radioisotope to a carbohydrate in the instant invention are largely dictated by the electronegativity of the radioisotope. Radioisotopes such as $^{18}$F having electronegativities and sizes similar to that of a hydroxyl group are readily substituted for a hydroxyl group of a carbohydrate. Carbon-11 is readily substituted for nonradioactive carbon within the carbohydrate or added thereto to form a cyanohydrin, ester, hemiacetal, acetal, or glycoside. The majority of radioisotopes of the instant invention are metals. The formation of a dative or covalent bond between a metallic radioisotope and the carbohydrate utilizes techniques of organometallic synthesis.

A metallic radioisotope is optionally bonded to the carbohydrate through an alcoholic oxygen linkage, a hemiacetal, or a linkage to the carbon backbone of the carbohydrate. Preferably, the metal ion is attached to the carbohydrate via an oxygen linkage. It is appreciated that additional small ligands may be bound to the metal ion in order to satisfy the radioisotope valency. It is further appreciated that the substitution of a metal radioisotope on a carbohydrate will render the resulting radioimaging agent much less likely to be metabolized by cellular enzymes. The limited degradation of the radioimaging agent assures that concentrations of the free radioisotope and the oxides thereof remain below toxic levels.

The radioisotope is directed to various bonding sites on the carbohydrate through the use of conventional carbohydrate chemistry techniques and purifications. The use of protecting groups such as acetals and ketals to effectively protect certain of the hydroxyl groups during reactions of carbohydrates is well known to the art. Through the use of reagents such as acetone and diethoxypropane under suitable reaction conditions, the radioisotope is directed to specific bonding sites on the carbohydrates. The radioisotopes are preferably bound to the carbohydrates of the instant invention at the C-2, C-3 or C-4 positions. In the cases of carbon-11 and fluorine-18, attachment at the C-4 position is preferred. It is recognized that steric considerations and cellular recognition of particular carbohydrate structures dictate the optimal location for attachment of a radioisotope of the instant invention. Thus, the metallic radioisotopes of the instant invention are preferably directed to attachment at the C-3 or C-4 positions of the carbohydrate.

Radioprotective moieties operative in the instant invention are wide ranging and merely required to inhibit free radical-chain reactions associated with exposure of cells to radiation. Radioprotective moieties operative in the instant invention illustratively include: ethiofos; aminoalkylaminoethanephosphorothialates, as taught in U.S. Pat. No. 5,167,947 which is incorporated herein by reference; and various pyridine tetryls which have been shown to be inhibitors of α-mannosidase as per U.S. Pat. No. 5,626,425, which is incorporated herein by reference. The radioprotective moieties of the instant invention are readily transported within cells by attachment to carbohydrates of the instant invention. In particular, D-glucose and epimers thereof are especially well suited for the delivery of radioprotective moieties. Owing to steric considerations, the radioprotective moiety is preferably attached to the carbohydrate at the C-6 position. In some instances, the radioprotective agent is attached to a single carbohydrate molecule while in other instances, it may be bonded to several carbohydrate molecules. Since glucose-like molecules readily are transported across cell membranes, the radioprotective agents of the instant invention effectively deliver radioprotection to cellular components and genetic sequences.

The rapid uptake of glucose-like molecules from the gastroenteral tract and bloodstream results in low plasma levels of the compounds of the instant invention, thereby decreasing the toxicity and enhancing effective distribution of the agents of the instant invention to tissues. It is appreciated that the agents of the instant invention are readily encapsulated in materials illustratively including enteric coatings, vesicles and liposomes. Encapsulation is optionally advantageous for example in preventing acid degradation, further enhancing cellular uptake by specific tissues; simultaneous delivery of multiple therapeutics, not all of which have a favorable uptake properties of the compounds of the instant invention; and modifying the cellular membrane transport mechanism. In particular, liposomal encapsulation optionally serves to selectively enhance uptake into the reticuloendothelial organs of liver, spleen and bone marrow. Other therapeutics that are optionally delivered with the compounds of the instant invention by means of vesicles or liposomes include conventional chemotherapeutic agents such as cis-platin, for the treatment of solid tumors and inflammatory lesions.

The agents of the instant invention may be administered in a suitable pharmaceutical carrier by a variety of routes including nasally, orally, intramuscularly, subcutaneously and intravenously. The agents of the instant invention are optionally administered together with an adjuvant, illustratively including mineral gels such as aluminum hydroxide, surface active substances such as lecithin, naturally occurring carbohydrates, peptides, oil emulsions and the like. The agents of the instant invention optionally are also administered in conjunction with conventional formulation aids, for example stabilizers, antioxidants, osmolality adjustment reagents, buffers, pH adjusting agents and the like. Where the agent is formulated for parenteral administration, a solution in a sterile physiologically acceptable medium, for example an isotonic or somewhat hypertonic aqueous solution is preferred. Agents of the instant invention are delivered to a patient in doses that serve their respective therapeutic function, yet owing to the efficient uptake of the agents at doses below the toxic level. For example, radioimaging agents are administered in doses ranging from 1 to 50 mg/kg and preferably ranging from 1 to 20 mg/kg. The radioprotective agents of the instant invention are delivered to patients in doses ranging from 20 to 400 mg/kg, and preferably in doses ranging from 50 to 250 mg/kg.

The methods and composition described above will be further understood with reference to the following nonlimiting examples.

EXAMPLE 1

Phosphorylation of Carbohydrate of the Instant Invention

Sixteen grams of glucose is dissolved in 160 milliliters of formamide and 32 milliliters of triethylamine. Eighty grams of reagent grade polyphosphoric acid is added and the resulting solution stirred at room temperature for 16 hours. Thereafter, the pH of the solution is raised to 9.0 using sodium hydroxide. The solution is then filtered using an Amicon YM-3 ultrafilter with the volume thereafter being reduced to about 40 milliliters through rotary evaporation. A crystalline precipitate is obtained through the addition of about 2 liters of 4° C. acetone. The resulting crystalline product is then redissolved in water and recrystallized. The resulting compound is characterized as 6'-phosphoroglucose.

EXAMPLE 2

Preparation of a Radioprotective Agent Containing a Phosphorothioic Acid

Reagent grade 2-(2-aminoethylamino) ethanol is purchased from Sigma Chemical Company (St. Louis, Mo., U.S.A.). Ten grams of this compound is solvated with 1 liter of 48% hydrobromic acid. The solution is refluxed for 1 hour and rotary evaporated to dryness. The resulting compound is filtered and recrystallized from methanol by the addition of acetone. The filtered and air dried product is characterized as N-(2-bromoethyl) alkanediamine hydrobromide.

The resulting product is dissolved in 200 milliliters of deionized water at 25° C. and added dropwise to 90 milliliters of 1 millimolar aqueous sodium thiophosphate, $Na_3PSO_3$. The resulting solution is then allowed to equilibrate in an ice bath and 145 milliliters of dimethylformamide (DMF) is added. The solution containing DMF and sodium thiophosphate is stirred for 12 hours at 30° C. A crystalline product is obtained from the reaction mixture by the addition of methanol. The crystalline product is redissolved in water and recrystallized through the subsequent addition of methanol. The filtered, washed with methanol and air dried product is characterized as the phosphorothioic acid ester of the starting compound.

The phosphorothioic acid ester having radioprotective properties is joined to a carbohydrate operative in the instant invention through the use of a phosphorylated carbohydrate. Sixteen grams of the carbohydrate-phosphate of Example 1 is mixed with 2.4 grams of 1-ethyl-(3,4-diethyl aminopropyl) carbodiimide and 2 grams of the phosphorothioic acid ester in about 40 milliliters of deionized water. The pH of the resulting solution is adjusted to 7.5 through the addition of sodium hydroxide. The solution is stirred for about 3 days at room temperature with the exclusion of light. The solution is filtered through an Amicon YM-3 ultrafilter and the volume of the solution reduced to about 10 milliliters through rotary evaporation. A radioprotective agent of the instant invention is precipitated from the reduced volume solution through the addition of 500 milliliters of 0° C. acetone. The radioprotective agent is collected on filter paper, redissolved in water and recrystallized through the addition of cold ethanol.

EXAMPLE 3

Phosphorylation of Carbohydrate of the Instant Invention 13.3 grams of ribose is dissolved in 160 milliliters of formamide and 32 milliliters of triethylamine. Eighty grams of reagent grade polyphosphoric acid is added and the resulting solution stirred at room temperature for 16 hours. Thereafter, the pH of the solution is raised to 9.0 using sodium hydroxide. The solution is then filtered using an Amicon YM-3 ultrafilter with the volume thereafter being reduced to about 40 milliliters through rotary evaporation. A crystalline precipitate is obtained through the addition of about 2 liters of 4° C. acetone. The resulting crystalline product is then redissolved in water and recrystallized. The resulting compound is characterized as 5'-phosphoroglucose.

EXAMPLE 4

Synthesis of Gadolinium Glucoside 6.9 grams (0.300 mole) of sodium were completely dissolved in a mixture of 200 ml of anhydrous isopropanol and 100 ml of tetrahydrofuran. 25.0 grams (0.0948 mole) of anhydrous ($H_2O$ content<100 ppm) of gadolinium trichloride was added in portions to the sodium isopropoxide solution. The resulting mixture was stirred at reflux for 5 hours. After 24 hours of sedimentation at room temperature, a transparent, colorless solution of gadolinium triisopropoxide in the alcohol-THF solution resulted. About 100 ml of the resultant solution were evacuated in Schlenk vessel and the dried residue was subsequently dissolved in 150 ml of deoxygenated, anhydrous, dimethylformamide. The remaining solution was analyzed for Gd(3) content by EDTA titration in the presence of urotropin buffer with xylenol orange as the metallochromic indicator.

90 ml of the DMF solution, having a concentration of 0.232 moles per liter (20.88 mM) were mixed in an inert atmosphere with 11.9 grams (66.05 mM) of anhydrous α-D-glucose in 92 ml of anhydrous DMF. The reaction mixture was heated for 30 minutes at 90–95° C. and then poured into 1.2 liters of dry chloroform. This produced a yellow precipitate which was separated on a glass filter (Schott No. 2), washed with 100 ml of chloroform and dried in vacuum at 100° C. The yield was 11.8 grams (81% of theoretical) of gadolinium glucoside, which has a formula as depicted in FIG. 1. It is known in the art that a number of radioactive isotopes of gadolinium are available. These include alpha emitters as well as beta emitters. Some particularly preferred isotopes comprise gadolinium 159 and gadolinium 162 as well as gadolinium 150 and 151. Also, as will be apparent to one of skill in the art, isotopes of other elements may be likewise incorporated in combination with carbohydrate materials.

Various modifications of the instant invention in addition to those shown and described therein will be apparent to those skilled in the art from the above description. Such modifications are also intended to fall within the scope of the appended claims.

What is claimed is:

1. A pharmaceutical composition for enhancing delivery of a radioprotective agent in vivo comprising:
   a) D-glucose which binds to, or penetrates a target cell, said D-glucose having attached thereto a an aminoalkylaminoethyl phosphorothioate free radical scavenger attached at the 6' position thereof; and
   b) a carrier suitable for delivery of said D-glucose to the target cell.

2. A radioimaging material comprising a gadolinium radioisotope chelated by a plurality of hexose monomers.

3. The radioimaging material of claim 2, wherein said gadolinium radioisotope is chelated by three glucose monomers.

4. A radioimaging material comprising a gadolinium radioisotope bonded to three glucose monomers through an oxygen on each glucose monomer at the 1' position thereof.

5. A radioimaging material comprising a glucoside of a gadolinium radioisotope, wherein said gadolinium radioisotope exhibits a square, bi-pyramidal coordination.

* * * * *